United States Patent

Stürmer et al.

[11] Patent Number: 5,919,961
[45] Date of Patent: Jul. 6, 1999

[54] CHIRAL COMPOUNDS

[75] Inventors: Rainer Stürmer, Roedersheim; Jun Okuda, Ingelheim, both of Germany; Kurt Ritter, Newton, Mass.

[73] Assignee: BASF Aktiengesellschaft, Ludwigshafen, Germany

[21] Appl. No.: 08/866,322

[22] Filed: May 30, 1997

[30] Foreign Application Priority Data

Jun. 3, 1996 [DE] Germany .................. 196 22 71

[51] Int. Cl.⁶ .................. C07F 17/00; C07F 11/00; C07F 7/28; C07C 209/00
[52] U.S. Cl. .................. 556/11; 556/7; 556/12; 556/14; 556/22; 556/26; 556/28; 556/43; 556/53; 534/15; 564/415; 564/489; 526/160; 526/443; 502/103; 502/117
[58] Field of Search .................. 556/7, 11, 12, 556/14, 22, 26, 28, 43, 53; 534/15; 564/415, 489

[56] References Cited

U.S. PATENT DOCUMENTS

| | | | |
|---|---|---|---|
| 4,634,775 | 1/1987 | Beck et al. .................. | 548/402 |
| 4,808,561 | 2/1989 | Welborn, Jr. .................. | 502/104 |
| 4,897,455 | 1/1990 | Welborn, Jr. .................. | 526/129 |
| 5,191,052 | 3/1993 | Welborn, Jr. .................. | 526/339 |
| 5,220,020 | 6/1993 | Buchwald et al. .................. | 544/106 |
| 5,264,405 | 11/1993 | Canich .................. | 502/103 |
| 5,292,893 | 3/1994 | Buchwald et al. .................. | 548/577 |
| 5,371,260 | 12/1994 | Sangokoya .................. | 556/171 |
| 5,391,793 | 2/1995 | Marks et al. .................. | 556/179 |
| 5,491,233 | 2/1996 | Buchwald et al. .................. | 544/174 |

FOREIGN PATENT DOCUMENTS

| | | |
|---|---|---|
| 151 282 | 8/1985 | European Pat. Off. . |
| 206 794 | 12/1986 | European Pat. Off. . |
| 269 395 | 6/1988 | European Pat. Off. . |
| 621 279 | 10/1994 | European Pat. Off. . |
| 633 264 | 1/1995 | European Pat. Off. . |
| 91/08738 | 6/1992 | WIPO . |

OTHER PUBLICATIONS

Organometallics, vol. 14, No. 2, (1995)–791.
Organometallics 1995, 14, 177–185, Ciruelos et al., American Chem. Soc.

Primary Examiner—Porfirio Nazario-Gonzalez
Attorney, Agent, or Firm—Keil & Weinkauf

[57] ABSTRACT

Chiral compounds of the formula I

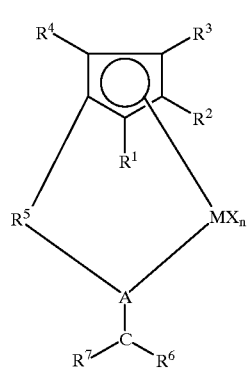

where the variables are as described in the specification.

8 Claims, No Drawings

CHIRAL COMPOUNDS

The present invention relates to chiral compounds of the formula I

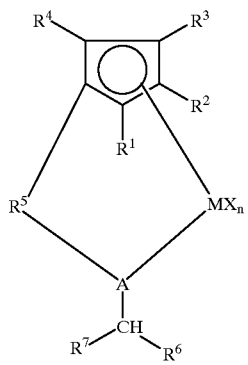

where
M is titanium, zirconium, hafnium, vanadium, niobium, tantalum or an element from the lanthanide series,
X is fluorine, chlorine, bromine, iodine, hydrogen, $C_1$- to $C_{10}$-alkyl, $C_6$- to $C_{15}$-aryl, alkylaryl having 1 to 10 carbon atoms in the alkyl radical and 6 to 20 carbon atoms in the aryl radical, $-OR^8$ or $-NR^8R^9$,
where
$R^8$ and $R^9$ are $C_1$- to $C_{10}$-alkyl, $C_6$- to $C_{15}$-aryl, alkylaryl, arylalkyl, fluoroalkyl or fluoroaryl, in each case having 1 to 10 carbon atoms in the alkyl radical and 6 to 20 carbon atoms in the aryl radical,
$R^1$ to $R^4$ are hydrogen, $C_1$- to $C_{10}$-alkyl, 5- to 7-membered cycloalkyl, which may itself carry a $C_1$- to $C_{10}$-alkyl as substituent, $C_6$- to $C_{15}$-aryl or arylalkyl, where, if desired, two adjacent radicals may also together be a saturated or unsaturated cyclic group having 4 to 15 carbon atoms, or $Si(R^{10})_3$, where
$R^{10}$ is $C_1$- to $C_{10}$-alkyl, $C_3$- to $C_{10}$-cycloalkyl or $C_6$- to $C_{15}$-aryl,

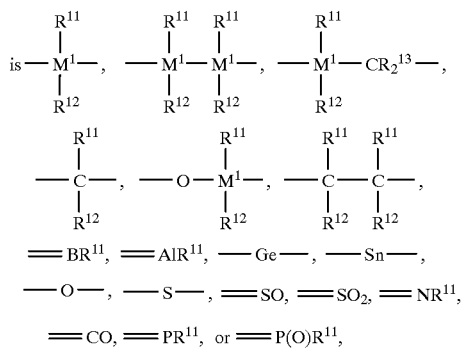

where
$R^{11}$, $R^{12}$ and $R^{13}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl, or where two adjacent radicals, in each case with the atoms connecting them, form a ring, and
$M^1$ is silicon, germanium or tin, A is boron, aluminum, gallium, indium, thallium, nitrogen, phosphorus, arsenic, antimony or bismuth,
$R^6$ and $R^7$ are different and are $C_1$- to $C_{10}$-alkyl, $C_6$- to $C_{15}$-aryl, alkylaryl or arylalkyl, in each case having 1 to 10 carbon atoms in the alkyl radical and 6 to 20 carbon atoms in the aryl radical, 5- to 7-membered cycloalkyl, which may itself be substituted by $C_1$- to $C_{10}$-alkyl or by groups containing hetero atoms,

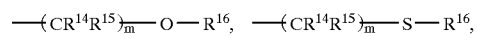

or $-CR^{17}R^{18}$, or where $R^6$ and $R^7$ together are a saturated or unsaturated cyclic group having 4 to 20 carbon atoms which may itself be substituted by $C_1$- to $C_{10}$-alkyl, $C_6$- to $C_{15}$-aryl, unsubstituted or substituted by hetero atoms, or by groups containing hetero atoms, $R^{14}$, $R^{15}$ and $R^{16}$ are hydrogen, $C_1$- to $C_{10}$-alkyl, $C_3$- to $C_{10}$-cyclo-alkyl or $C_6$- to $C_{15}$-aryl,
$R^{17}$ and $R^{18}$ are $C_3$- to $C_{10}$-cycloalkyl, $C_6$- to $C_{15}$-aryl or groups containing hetero atoms,
m is an integer in the range from 1 to 4, and n corresponds to the valence of M minus 2.

The present invention furthermore relates to a process for the preparation of these chiral compounds, to their use as active catalyst component for enantioselective hydrogenation, and to a process of enantioselective hydrogenation.

For the synthesis of optically active compounds and chiral intermediates, enantioselective hydrogenation using rhodium or ruthenium complexes as catalysts is very important, as described in EP-A 151 282 and der EP-A 269 395. However, these rhodium and ruthenium complexes can only be obtained by complex processes.

U.S. Pat. No. 5,292,893, U.S. Pat. No. 5,220,020 and WO 92/09545 describe titanium compounds as catalysts for enantioselective hydrogenation. These compounds can likewise only be prepared by a complex process and in addition must be subjected to racemate separation, during which at least 50% of the substance is lost.

The compounds known hitherto which can be employed as catalysts for enantioselective hydrogenation make industrial utilization difficult and uneconomic.

It is an object of the present invention to provide novel compounds which can be employed as catalysts for enantioselective hydrogenation and which do not have the above-mentioned disadvantages and in particular can be prepared by simple processes.

We have found that this object is achieved by the chiral compounds of the formula I described at the outset.

We have furthermore found a process for the preparation of such chiral compounds, their use as active catalyst component for enantioselective hydrogenation, and a process for enantioselective hydrogenation.

Of the chiral compounds of the formula I

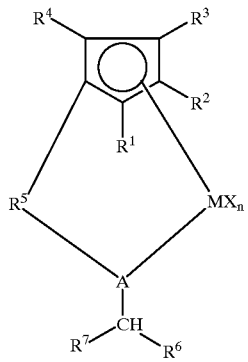

preference is given to those in which

M is titanium, zirconium or hafnium, in particular titanium,

X is chlorine, $C_1$- to $C_4$-alkyl or phenyl, where the radicals X may be identical or different, but are preferably identical, $R^1$ to $R^4$ are hydrogen or $C_1$- to $C_4$-alkyl, or where two adjacent radicals are a saturated or unsaturated group having 4 to 10 carbon atoms, for example indenyl, tetrahydroindenyl or benzindenyl, which may be substituted or unsubstituted,

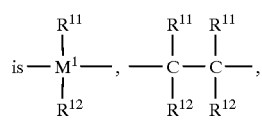

in particular —Si(CH$_3$)$_2$— or —CH$_2$—CH$_2$—, or alternatively —Si(C$_6$H$_5$)$_2$— or —C(CH$_3$)H—CH$_2$—, A is boron, aluminum, nitrogen or phosphorus, preferably boron, nitrogen or phosphorus, in particular nitrogen, $R^6$ and $R^7$ confer chirality on the compound and are $C_1$- to $C_{10}$-alkyl, preferably $C_1$- to $C_4$-alkyl, in particular methyl, ethyl, isopropyl, sec-butyl or tert-butyl, $C_6$- to $C_{12}$-aryl, in particular phenyl, alkylaryl, in particular tolyl, cyclopentyl, cyclohexyl or amino-substituted cyclohexyl, —CH$_2$OR$^{16}$ or —C(CH$_3$)HOR$^{16}$, —CH$_2$SR$^{16}$ or —CH$_2$—CH$_2$—SR$^{16}$ or —C(C$_6$H$_{11}$)(NHRNR$_2$), or where $R^6$ and $R^7$ together are a cyclic group, preferably phenyl, cyclohexyl, naphthalenyl or substituted naphthalenyl.

Particularly preferred

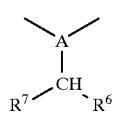

groups are:

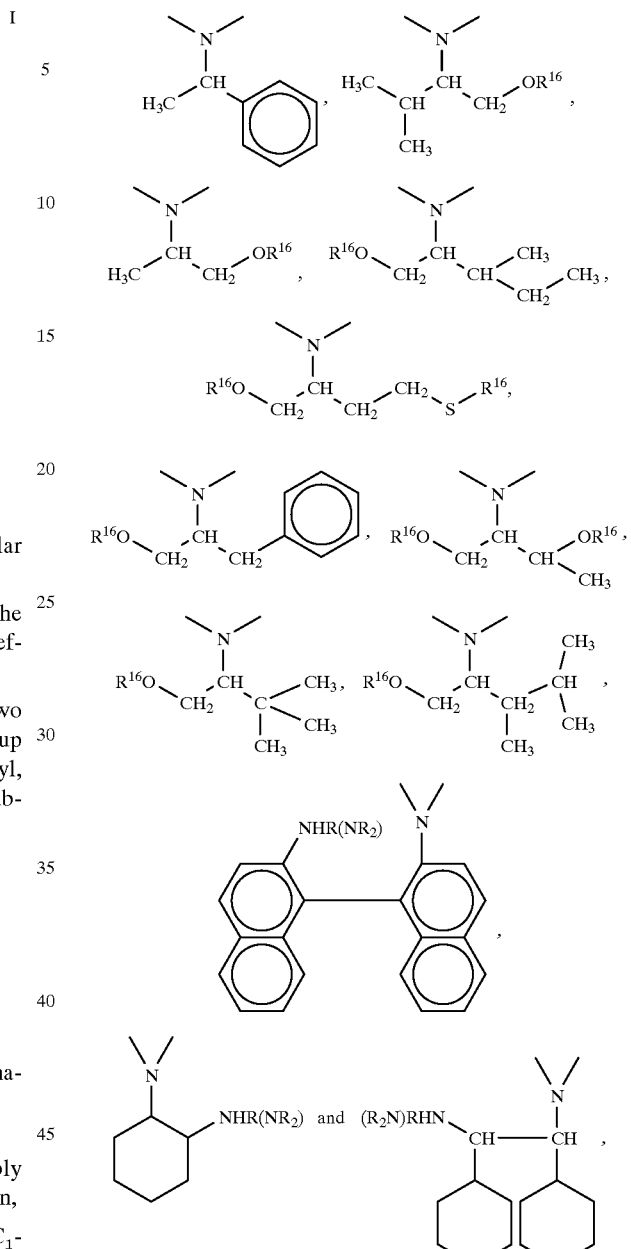

in both enantiomeric forms and, in the case of compounds having further centers of chirality, the respective diastereomers and enantiomers.

The radicals R in these preferred groups are preferably methyl, ethyl, tert-butyl, benzyl, tert-butyloxycarbonyl, benzyloxycarbonyl or p-methoxybenzyl.

The novel chiral compounds of the formula I can be prepared by reacting the appropriately substituted cyclopentadienyl radicals with $R^5Z_2$ and $MX_n$, where Z is fluorine, chlorine, bromine or iodine, and subsequently with

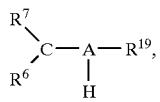

where
- $R^{19}$ is hydrogen, an alkali metal, preferably lithium, or $M^1Y$, where $M^1$ is an alkaline earth metal, preferably magnesium and Y is fluorine, chlorine, bromine or iodine.

The individual steps in these reactions are known per se and are described, for example, in organometallics, 14, (1995), 791. The reaction conditions are not crucial per se; the temperatures are generally in the range from −78 to 50° C., preferably 0 to 30° C.

However, the novel sequence of the individual steps in these reactions has the advantage of a higher yield.

The novel chiral compounds of the formula I can be employed as active catalyst component for enantioselective hydrogenation.

Suitable cocatalysts are aryloxyalumoxanes, as described in U.S. Pat. No. 5,391,793, aminoaluminoxanes, as described in U.S. Pat. No. 5,371,260, aminoaluminoxane hydrochlorides, as described in EP-A 633 264, siloxyaluminoxanes, as described in EP-A 621 279, or mixtures thereof.

It is also possible to employ metal compounds, such as alkyllithium, alkylmagnesium and alkylaluminum compounds, preferably n-butyllithium, n-butyl-n-octylmagnesium, n-butyl-n-heptylmagnesium, tri-n-hexylaluminum, triisobutylaluminum, triethylaluminum, trimethylaluminum and ethylmagnesium chloride, as cocatalysts.

Preference is given to n-butyllithium, ethylmagnesium chloride and methylaluminoxanes.

It is possible to employ mixtures of various cocatalysts and also mixtures of various chiral compounds of the formula I.

The amount of chiral compounds of formula I is preferably in the range from 0.001 mol % to 50 mol %, preferably from 0.01 to 10 mol %, in particular from 0.02 to 1 mol %, based on the compound to be hydrogenated.

The amount of cocatalyst is preferably in the range from 0.01 to 50 mol equivalents, preferably from 0.5 to 2.5 mol equivalents, in particular from 1.5 to 2.0 mol equivalents, based on the amount of chiral compound of the formula I.

The catalyst can also be employed in supported form; support materials which may be mentioned are aluminosilicates, silicon dioxides, such as silica gels or kieselguhr, activated charcoal, aluminum oxides, zeolites or Celite. Processes for supporting catalysts are known per se and are described, for example, in EP-A 206 794.

It is also possible to add additives which are capable of stabilizing the active catalyst components, such as silanes, preferably having at least one hydrogen substituent, such as polym ric hydridosilanes, polymeric tin hydrides or trialkyltin hydrides. Preference is given to phenylsilane, tri-n-butyl- and tri-n-octyltin hydride. If such an additive is used, the amount thereof is preferably from 0.1 to 1000 mol equivalents, preferably from 1 to 10 mol equivalents, based on the amount of chiral compound of the formula I.

Suitable compounds for hydrogenation are all those which contain a double bond, for example C=O, C=N or C=C, having one or more substituents. Preference is given to acyclic and cyclic imines, mono-, di- and trisubstituted olefins, azines, hydrazones, oxime ethers, allyl ethers, allyl alcohols, enamines, enamides, oxazolones and ketones. Allyl alcohols and ketones are preferably hydrogenated in the presence of alkyl- or arylsilanes as additives. Such compounds and their use in hydrogenation are known per se and described, for example, in U.S. Pat. No. 5,292,893 and U.S. Pat. No. 5,491,233. Preference is given to acyclic and cyclic imines.

Enantioselective hydrogenation using the novel chiral compounds of the formula I as catalyst component is preferably carried out in solution. Suitable solvents are all solvents which are stable toward organometallic compounds, for example hydrocarbons and acyclic and cyclic ethers, such as tetrahydrofuran, toluene, diethyl ether, heptane, hexane, methyl tert-butyl ether, dioxane, petroleum ether, dimethyl ether and benzene, in particular tetrahydrofuran, toluene, heptane and mixtures thereof. If liquid compounds are hydrogenated, it is also possible to work without a solvent.

Enantioselective hydrogenation reactions are known per se. They are usually carried out at a pressure in the range from 1 to 1000 bar, preferably from 10 to 500 bar, and at a temperature in the range from −10 to 250° C., preferably from 20 to 150° C., in particular from 40 to 90° C.

Enantioselective hydrogenation reactions can be carried out continuously or batchwise in any pressure reactor.

In a preferred procedure, the novel chiral compound of the formula I is mixed with a solvent, and the cocatalyst is added at room temperature. The compound to be hydrogenated is then added and hydrogenated using hydrogen over a period of from 3 to 48 hours. The reactor is then decompressed, the solvent removed and the resultant hydrogenated compound purified.

If an additive is used, this is preferably added directly after the cocatalyst.

The novel chiral compounds of the formula I are simple to prepare, requiring no racemate separation or enrichment of one enantiomer, and are suitable as catalyst component in enantioselective hydrogenation, allowing an enantiomeric excess of up to 99%, in some cases even more, to be achieved, thus providing an extremely economical and industrially suitable hydrogenation process. Furthermore, it is possible to employ a wide range of compounds for enantioselective hydrogenation.

EXAMPLES

EXAMPLE 1

Preparation of {η5; η1-[1-(1'-(1R)-methylbenzyl-amido)dimethylsilyl]cyclopentadienyl}titanium dichloride (I1)

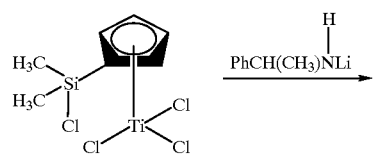

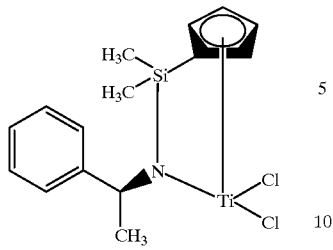

15.0 mmol of chlorodimethylsilylcyclopentadienyltitanium (III) chloride (Royo et. al.; organometallics, 1995, 177) were dissolved in 150 ml of ether, and 15 mmol of triethylamine were added. A solution of lithium (1R)-1-phenylethylamide in 180 ml of THF/ether (1:1) was then cooled to −78° C. and added dropwise to the titanium complex solution, which had likewise been cooled to −78° C. The mixture was strirred at this temperature for 30 minutes and at RT for 2 hours. The batch was filtered, the solvent was removed, and the residue was recrystallized from ether, giving the titanium complex I1 in a yield of 72%; 4.10 g of yellow prisms.

Spectroscopic data:

400MHz H-NMR ($C_6D_6$) −0.48 (s, 3H); 0.08 (s, 3H); 1.50 (d, J=6.8 Hz, 3H); 5.99–6.04 (m, 2H); 6.47–6.50 (m, 2H); 6.52 (q, J=6.8 Hz, 1H), 7.02 (m, 3H), 7.27 (m, 2H)

100 MHz C-NMR ($C_6D_6$):

−3.11; −0.69; 0.92; 19.12; 64.63; 109.51; 124.12; 124.44; 126.06; 126.11; 127.26; 128.06; 128 .80; 144.10

MS (EI)

m/z: 106 (58%); 241 (38%) 344; (100%); 346 (68%)

Elemental analysis:

$C_{15}H_{19}Cl_2NSiTi$ (360.2) Calc. C 50.00 H 5.32 N 3.89 Found C 49.87 H 5.31 N 3.79

Optical rotation:

Complex of 1R-1-phenylethylamine: +344.1° (589 nm, 22° C., c=1 in diethyl ether)

Complex of 1S-1-phenylethylamine: −344.1° (589 nm, 22° C., c=1 in diethyl ether)

EXAMPLE 2

The enantiomeric complex of (1S)-1-phenylethylamine was prepared analogously.

EXAMPLE 3

Enantioselective hydrogenation 0.1mmol of the complex Ii from Example 1 was dissolved in 20 ml of toluene under argon in a Schlenk tube, and 0.2 mmol of n-BuLi were added dropwise at RT. The initially orange solution became brown; it was then stirred at RT for 5 minutes, and 100 mmol of the N-benzylimine of acetophenone was added in one portion (substrate/catalyst ratio 1000:1). The resultant solution was transferred into an autoclave and stirred for 12 hours at 80° C. and a hydrogen pressure of 150 bar. The autoclave was decompressed, the reaction mixture was freed from solvent, and the oily residue was distilled in a bulb tube, giving 92 mmol (92%) of (1R)-N-benzyl-1-phenylethylamine as a colorless oil. After trifluoroacetylation, the enantiomeric excess was determined by gas chromatography as being ee=12%.

We claim:

1. A chiral compound of the formula I

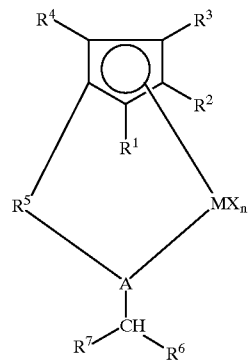

where

M is titanium, zirconium, hafnium, vanadium, niobium, tantalum or an element from the lanthanide series, X is fluorine, chlorine, bromine, iodine, hydrogen, $C_1$- to $C_{10}$-alkyl, $C_6$- to $C_{15}$-aryl, alkylaryl having 1 to 10 carbon atoms in the alkyl radical and 6 to 20 carbon atoms in the aryl radical, —$OR^8$ or —$NR^8R^9$, where $R^8$ and $R^9$ are $C_1$- to $C_{10}$-alkyl, $C_6$- to $C_{15}$-aryl, alkylalkyl, arylalkyl, fluoroalkyl or fluoroaryl, in each case having 1 to 10 carbon atoms in the alkyl radical and 6 to 20 carbon atoms in the aryl radical, $R^1$ to $R^4$ are hydrogen, $C_1$- to $C_{10}$-alkyl, 5-to 7-membered cycloalkyl, which may itself carry a $C_1$- to $C_{10}$-alkyl as substituent, $C_6$- to $C_{15}$-aryl or arylalkyl, where, if desired, two adjacent radicals may also together be a saturated or unsaturated cyclic group having 4 to 15 carbon atoms, or $Si(R^{10})_3$, where $R^{10}$ is $C_1$- to $C_{10}$-alkyl, $C_3$- to $C_{10}$-cycloalkyl or $C_6$- to $C_{15}$-aryl,

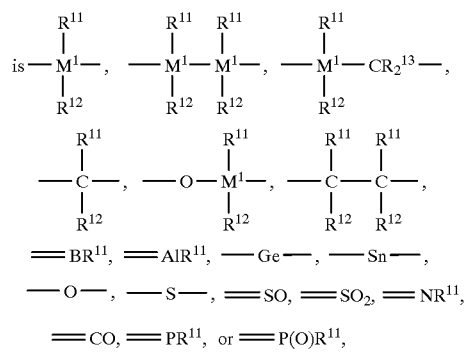

where $R^{11}$, $R^{12}$ and $R^{13}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl, or where two adjacent radicals, in each case with the atoms connecting them, form a ring, and $M^1$ is silicon, germanium or tin, A is boron, aluminum, gallium, indium, thallium, nitrogen, phosphorus, arsenic, antimony or bismuth, $R^6$ is selected from the group consisting of $C_1$- to $C_{10}$-alkyl, $C_6$- to $C_{15}$-aryl, alkylaryl or arylalkyl, in each case having 1 to 10 carbon atoms in the alkyl radical and 6 to 20 carbon atoms in the aryl radical, 5- to 7-membered cycloalkyl, which may itself be substituted by $C_1$- to $C_{10}$-alkyl or by groups containing hetero atoms,

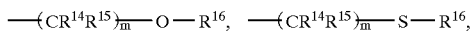

and —$CR^{17}R^{18}$; and $R^7$ is selected from the group consisting of isopropyl, sec-butyl or tert-butyl, $C_6$-to $C_{15}$-aryl, alkylaryl or arylalkyl, in each case having 1 to 10 carbon atoms in the alkyl radical and 6 to 20 carbon atoms in the aryl radical, 5- to 7-membered cycloalkyl, which may itself be substituted by $C_1$- to $C_{10}$-alkyl or by groups containing hetero atoms,

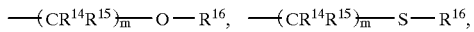

and —$CR^{17}R^{18}$;

or where $R^6$ and $R^7$ together form a saturated or unsaturated cyclic group having 4 to 20 carbon atoms which may itself be substituted by $C_1$- to $C_{10}$-alkyl, $C_6$- to $C_{15}$-aryl, unsubstituted or substituted by hetero atoms, or by groups containing hetero atoms;

$R^{14}$, $R^{15}$ and $R^{16}$ are hydrogen, $C_1$- to $C_{10}$-alkyl, $C_3$- to $C_{10}$-cycloalkyl or $C_6$- to $C_{15}$-aryl, $R^{17}$ and $R^{18}$ are $C_3$- to $C_{10}$-cycloalkyl, $C_6$- to $C_{15}$-aryl or groups containing hetero atoms, m is an integer in the range from 1 to 4, and n corresponds to the valence of M minus 2.

2. A chiral compound as claimed in claim 1, where M in the formula I is titanium, zirconium or hafnium.

3. A chiral compound as claimed in claim 1, where A in the formula I is boron, nitrogen or phosphorus.

4. A process for the preparation of a chiral compound of the formula I as claimed in claim 1, which comprises reacting an appropriately substituted cyclopentadienyl radical with $R^5Z_2$ and $MX_n$, where Z is fluorine, chlorine, bromine or iodine, and subsequently with

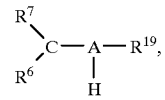

where $R^{19}$ is hydrogen, an alkali metal or $M^1Y$,
where $M^1$ is an alkaline earth metal and
Y is fluorine, chlorine, bromine or iodine.

5. A method of using a chiral compound of the formula I as claimed in claim 1 as active catalyst component for enantioselective hydrogenation.

6. A method of using a chiral compound as claimed in claim 5 in the presence of a cocatalyst.

7. A method of using a chiral compound as claimed in claim 5 or 6 for enantioselective hydrogenation of imines.

8. A process for the enantioselective hydrogenation of imines, which comprises working in solution and using, as active catalyst component, a chiral compound of the formula I as claimed in claim 1.

* * * * *